(12) United States Patent
Lee et al.

(10) Patent No.: US 7,041,823 B2
(45) Date of Patent: May 9, 2006

(54) PROCESS FOR PREPARING 9-[4-ACETOXY-3-(ACETOXYMETHYL)BUT-1-YL]-2-AMINOPURINE

(75) Inventors: Byoung-suk Lee, Seoul (KR); Sang-hoon Shin, Gwacheon (KR); Jong-sik Park, Seoul (KR)

(73) Assignee: Kyungdong Pharm. Co., Ltd., (KR)

( * ) Notice: Subject to any disclaimer, the term of this patent is extended or adjusted under 35 U.S.C. 154(b) by 0 days.

(21) Appl. No.: 10/521,352

(22) PCT Filed: Jul. 15, 2003

(86) PCT No.: PCT/KR03/01396

§ 371 (c)(1),
(2), (4) Date: Jan. 12, 2005

(87) PCT Pub. No.: WO2004/007497

PCT Pub. Date: Jan. 22, 2004

(65) Prior Publication Data

US 2005/0222413 A1    Oct. 6, 2005

(30) Foreign Application Priority Data

Jul. 15, 2002    (KR) ...................... 10-2002-0041267

(51) Int. Cl.
*C07D 473/32*    (2006.01)
(52) U.S. Cl. ...................................................... 544/277
(58) Field of Classification Search ................. 544/277
See application file for complete search history.

(56) References Cited

U.S. PATENT DOCUMENTS

| | | | | |
|---|---|---|---|---|
| 5,138,057 A | * | 8/1992 | Geen et al. | 544/277 |
| 5,684,153 A | * | 11/1997 | Geen et al. | 544/276 |
| 5,917,041 A | * | 6/1999 | Daluge et al. | 544/264 |

\* cited by examiner

*Primary Examiner*—Kamal A. Saeed
(74) *Attorney, Agent, or Firm*—Galgano & Burke, LLP

(57) ABSTRACT

Disclosed is a process for preparing 9-[4-acetoxy-3-(acetoxymethyl)but-1-yl]-2-aminopurine (called Famciclovir), a drug of purine derivatives having antiviral activity. This process comprises reacting 2-aminopurine with 2-acetoxymethyl-4-bromobut-1-yl-acetate in the presence of thallium (I) ethoxide to give the desired compound. According to this process, the desired compound can be prepared in very high selectivity and purity under mild reaction conditions.

4 Claims, No Drawings

PROCESS FOR PREPARING 9-[4-ACETOXY-3-(ACETOXYMETHYL)BUT-1-YL]-2-AMINOPURINE

TECHNICAL FIELD

The present invention relates to a process for preparing 9-[4-acetoxy-3-(acetoxymethyl)but-1-yl]-2-aminopurine (called Famciclovir) of Formula (I), a drug of purine derivatives having antiviral activity:

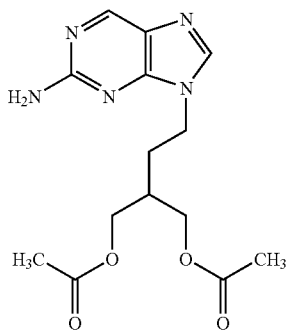

(I)

More particularly, the present invention relates to a novel process for preparing 9-[4-acetoxy-3-(acetoxymethyl)but-1-yl)-2-aminopurine (called Famciclovir) of Formula (I), a drug of purine derivatives having antiviral activity, in which 2-aminopurine of Formula (II) is reacted with 2-acetoxymethyl-4-bromobut-1-yl-acetate of Formula (III) in the presence of thallium (I) ethoxide to give the compound of Formula (I) in high selectivity while minimizing the production of 7-(4-acetoxy-3-(acetoxymethyl)but-1-yl]-2-aminopurine of Formula (V), a reaction byproduct:

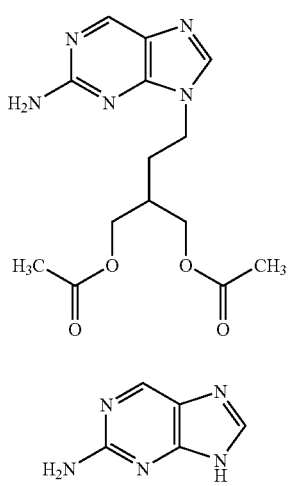

(I)

(II)

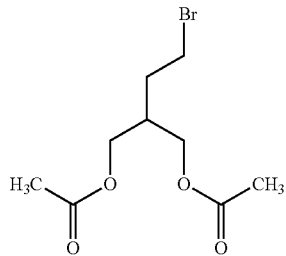

(III)

TlOEt (IV)

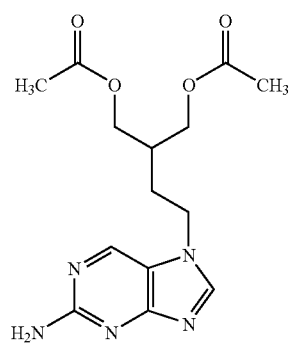

(V)

BACKGROUND ART

Prior techniques for preparing the compound of Formula (I) are disclosed in European Patent No. 182,024, and U.S. Pat. Nos. 5,684,153, 5,138,057 and 5,917,041.

Among the above prior patents, EP No. 182,024 and U.S. Pat. No. 5,684,153 discloses a process for preparing 9-[4-acetoxy-3-(acetoxymethyl)but-1-yl]-2-aminopurine of Formula (I), in which 2-amino-6-chloropurine of Formula (VI) is reacted with 2-acetoxymethyl-4-halobut-1-yl-acetate of Formula (VII) to give 9-[4-acetoxy-3-(acetoxymethyl)but-1-yl]-2-amino-6-chloropurine of Formula (VIII), which is then reduced into the compound of Formula (I) in the presence of palladium, as shown in Scheme 1 below.

Scheme 1:

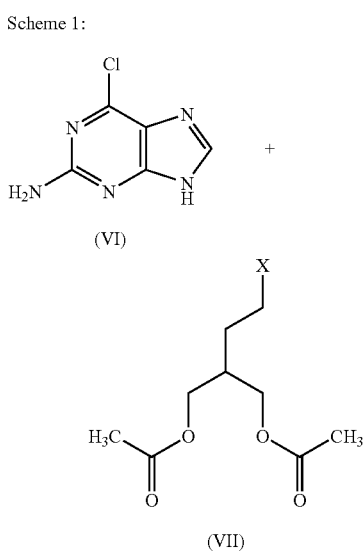

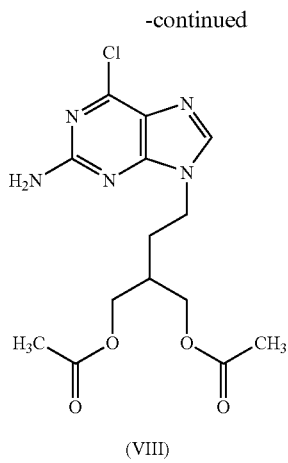

(VIII)

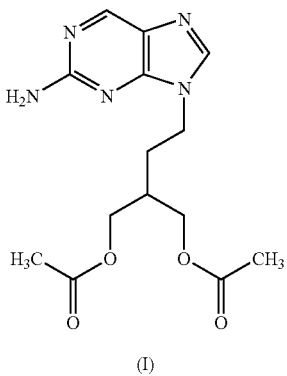

(I)

wherein X is a halogen atom.

However, the prior process according to Scheme 1 has problems in that the compound of Formula (VIII) and 7-[4-acetoxy-3-(acetoxymethyl)but-1-yl]-2-amino-6-chloropurine of Formula (IX) as a byproduct are produced from the compound of Formula (VI) and the compound of Formula (VII) at a ratio of 80%:20%, as shown in Scheme 2 below, so that selectivity for the compound of Formula (VIII) is low and the purification of the compound of Formula (VIII) is very difficult.

Scheme 2:

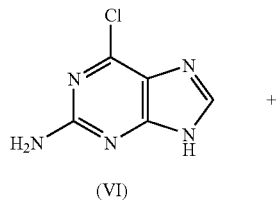

(VI)

(VII)

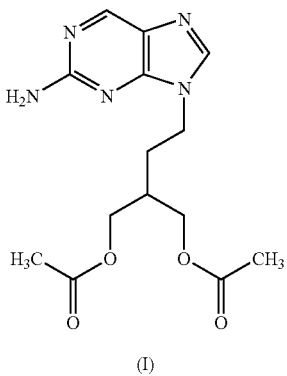

(VIII)  :  (IX)
80%  :  20% wherein X is a halogen atom.

Furthermore, the process according to Scheme 1 above has problems in that it requires the use of highly explosive palladium in the preparation of the compound of Formula (I) as the desired compound from the compound of Formula (VIII), and thus, is inefficient and unsuitable for industrial application.

Moreover, U.S. Pat. No. 5,138,057 discloses a process for preparing 9-[4-acetoxy-3-(acetoxymethyl)but-1-yl]-2-aminopurine of Formula (I), in which 2-amino-6,8-dichloropurine of Formula (X) is reacted with 2-acetoxymethyl-4-halobut-1-yl-acetate of Formula (VII) to give 9-[4-acetoxy-3-(acetoxymethyl)but-1-yl]-2-amino-6,8-dichloropurine of Formula (XI) which is then reduced under a pressurized condition in the presence of palladium, as shown in Scheme 3 below.

Scheme 3:

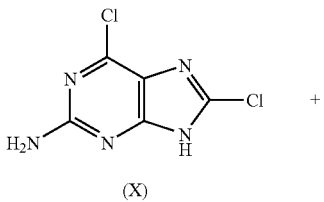

(X)

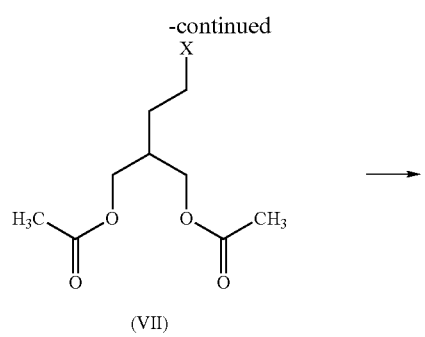

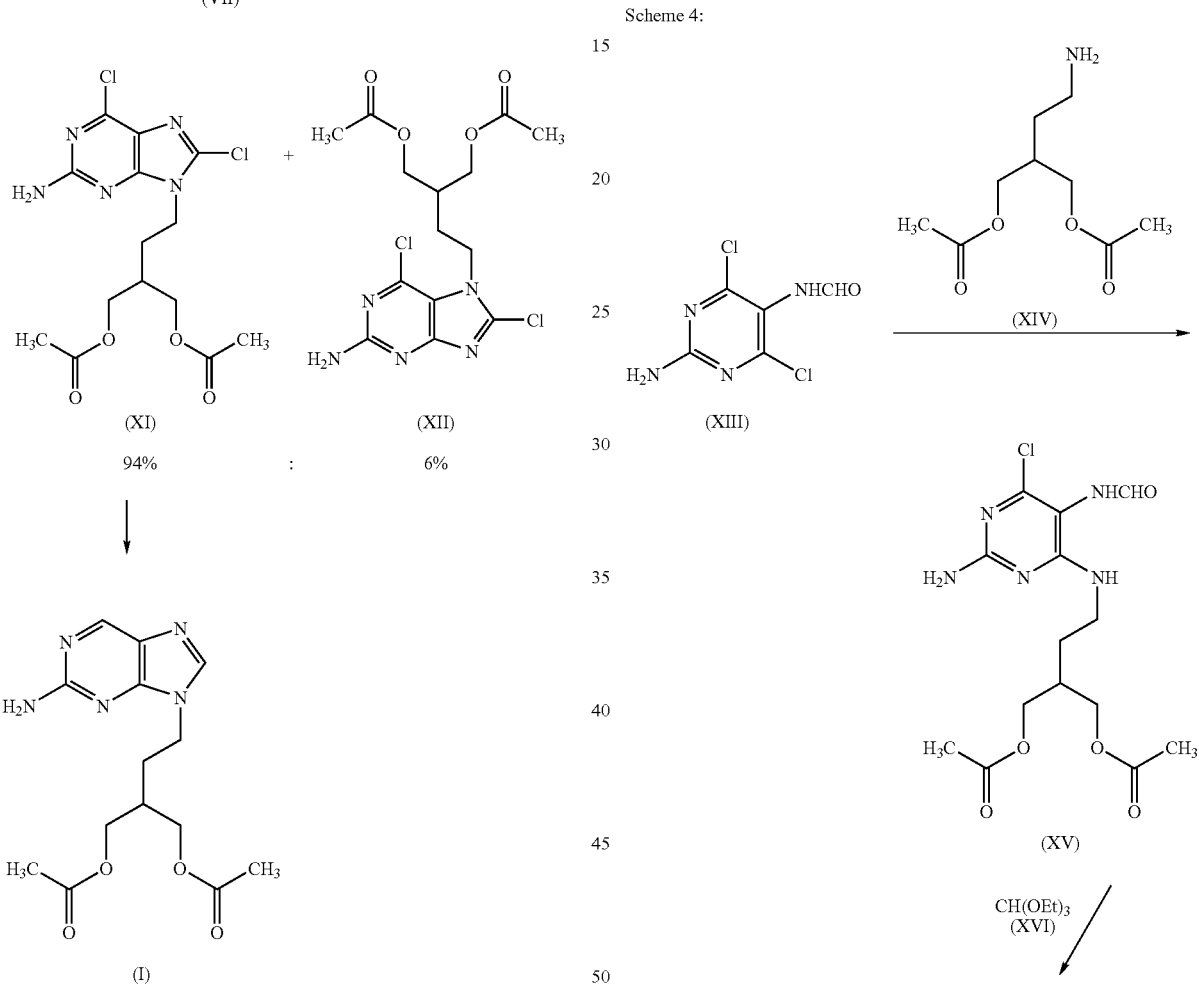

aminourine of Formula (I), in which N-(2-amino-4,6-dichloro-5-pyrimidinyl)formamide of Formula (XIII) is reacted with 2-acetoxymethyl-4-aminobut-1-yl-acetate of Formula (XIV) to give a compound of Formula (XV) which is then converted into 9-[4-acetoxy-3-(acetoxymethyl)but-1-yl]-2-amino-6-chloropurine of Formula (VIII) by means of triethylorthoformate of Formula (XVI), and then the compound of Formula (VIII) is reduced into the compound of Formula (I) in the presence of palladium, as shown in Scheme 4 below.

Scheme 4:

However, the process according to Scheme 3 shows relatively high selectivity for the compound of Formula (XI), since the compound of Formula (XI) and 7-[4-acetoxy-3-(acetoxymethyl)but-1-yl]-2-amino-6,8-dichloropurine of Formula (XII) as a reaction byproduct are produced from the compound of Formula (X) and the compound of Formula (VII) at a ratio of 94%:6%. However, this process has problems in that it requires the use of highly explosive palladium in the production of the compound of Formula (I) as the desired product from the compound of Formula (XI), as in EP No. 182,024 and U.S. Pat. No. 5,684,153, and needs to be carried out under a pressurized condition higher than 50 psi, thus posing difficulty in industrial application.

In addition, U.S. Pat. No. 5,917,041 discloses a process for preparing 9-[4-acetoxy-3-(acetoxymethyl)but-1-yl]-2-

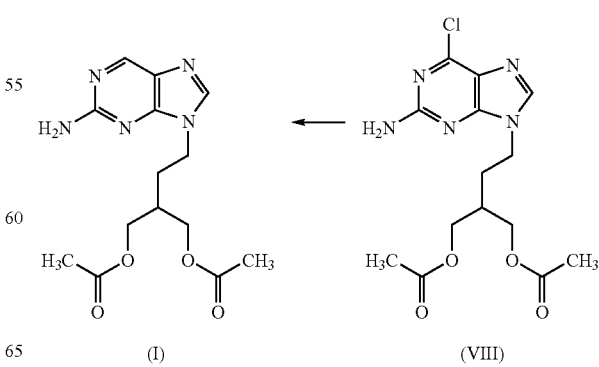

However, the process according to Scheme 4 has problems in that it requires the use of expensive 2,5-diamino-4,6-dihydroxypyrimidine of Formula (XVII) and expensive chloromethylene iminium salt of Formula (XVIII) in the production of the compound of Formula (XIII) as a starting material, as shown in Scheme 5 below, and gives the compound of Formula (I) as the desired product at a very low yield of about 32% via several steps from the compound of Formula (XVII), and also requires the use of highly explosive palladium as in EP No. 182,024 and U.S. Pat. No. 5,684,153 as described above, so that it utilizes a long reaction route and is inefficient and thus has a difficulty in industrial application.

Scheme 5:

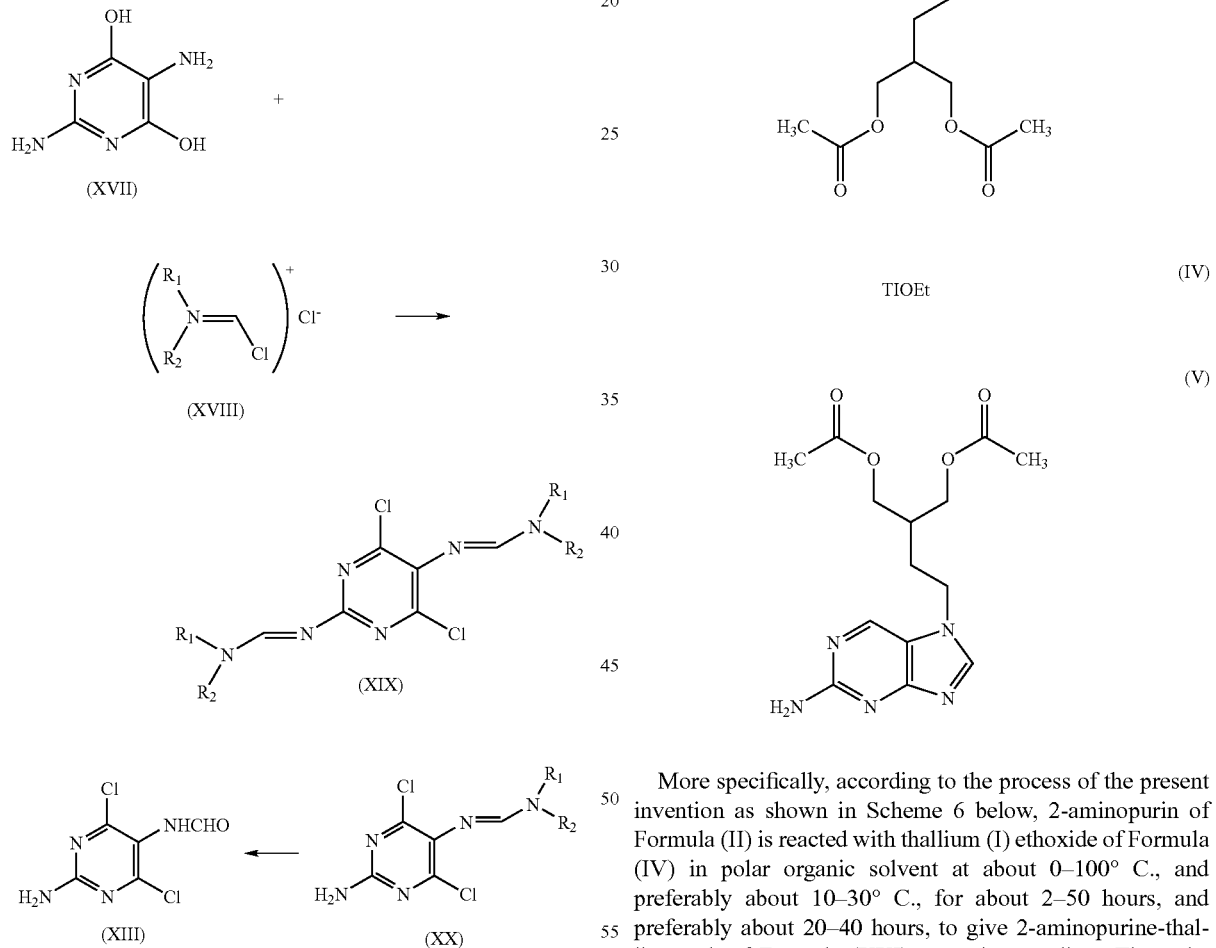

Thus, in the relevant field of art, there has been demanded the development of a process which allows the preparation of 9-[4-acetoxy-3-(acetoxymethyl)but-1-yl]-2-aminopurine (called Famciclovir), a drug of purine derivatives having antiviral activity, at high selectivity under mild reaction conditions, while minimizing the production of 7-[4-acetoxy-3-(acetoxymethyl)but-1-yl]-2-aminopurine as a reaction byproduct.

DISCLOSURE OF THE INVENTION

According to a preparing process of the present invention, owing to the introduction of thallium (I) ethoxide critical to this process, 9-[4-acetoxy-3-(acetoxymethyl)but-1-yl]-2-aminopurine (called Famciclovir) of Formula (I), a drug of purine derivatives having antiviral activity, can be prepared in a very high selectivity of 98% while minimizing the production of 7-[4-acetoxy-3-(acetoxymethyl)but-1-yl]-2-aminopurine of Formula (V) as a reaction byproduct:

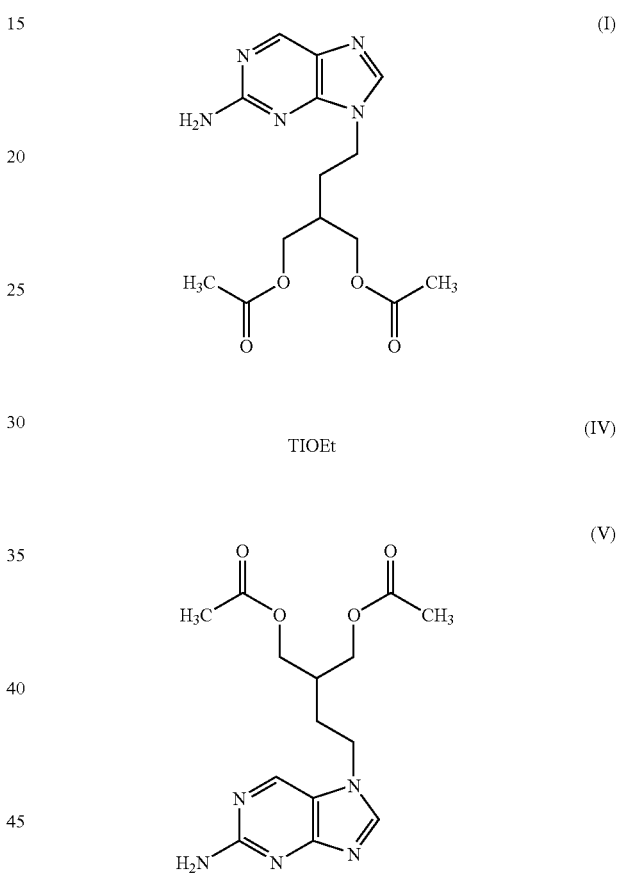

More specifically, according to the process of the present invention as shown in Scheme 6 below, 2-aminopurin of Formula (II) is reacted with thallium (I) ethoxide of Formula (IV) in polar organic solvent at about 0–100° C., and preferably about 10–30° C., for about 2–50 hours, and preferably about 20–40 hours, to give 2-aminopurine-thallium salt of Formula (XXI) as an intermediate. Then, the compound of Formula (XXI) is reacted with 2-acetoxy-4-bromobut-1-yl-acetate of Formula (III) in polar organic solvent at about 0–100° C., and preferably about 10–30° C., for about 50–200 hours, and preferably about 70–100 hours, to give Famciclovir of Formula (I) as the desired compound. Moreover, according to the process of the present invention, since Famciclovir of Formula (I) and 7-[4-acetoxy-3-(acetoxymethyl)but-1-yl]-2-aminopurine of Formula (V) as a reaction product are produced at a ratio of 98%:2%, the desired compound can be prepared in very high selectivity.

Scheme 6:

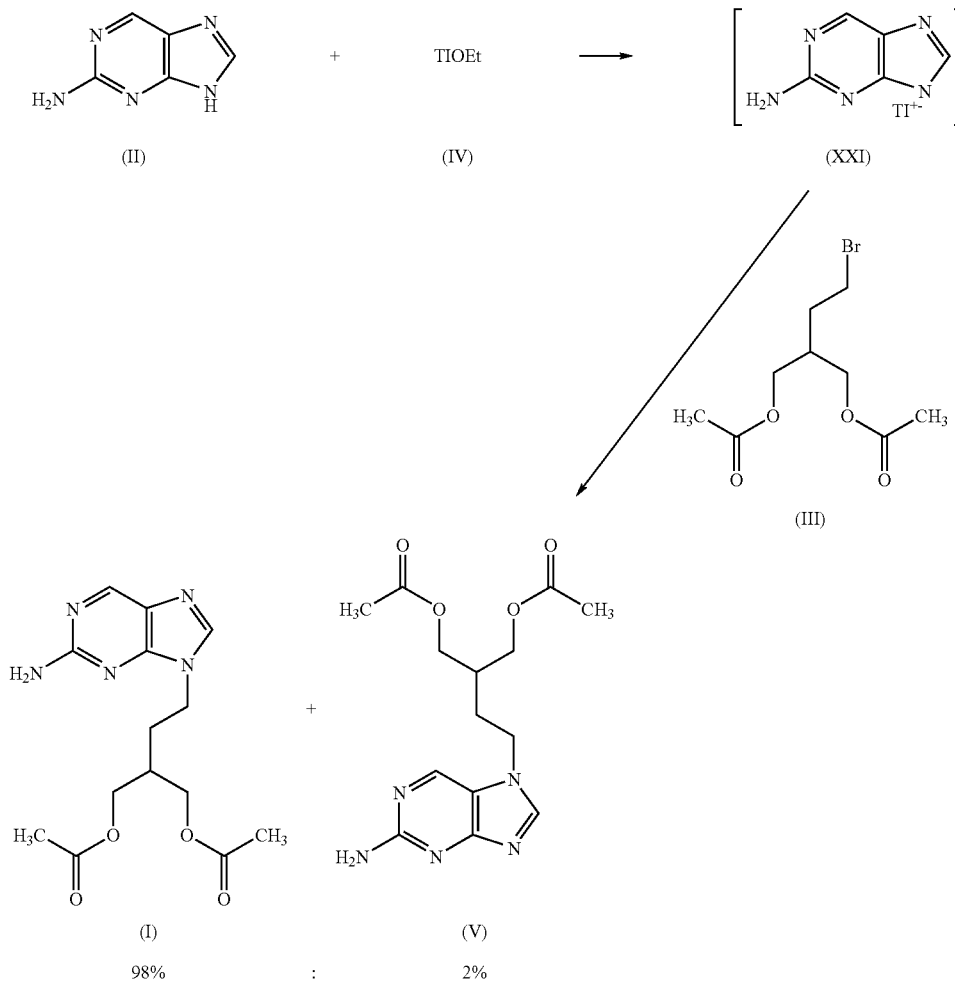

The compound of Formula (II), which is used as the starting material in the process of the present invention, is commercially available or can be produced according to methods described in, for example, *Heterocycles,* 17, 405 (1982) and *Journal of the Chemistry Society,* 2060 (1954). Also, the compound of Formula (III), a branched hydrocarbon, which is used as the starting material in the process of the present invention, can be prepared according to the conventional method, such a method described in European Patent Publication No. 141,927.

Preferred examples of the polar organic solvent, which can be used in the preparing process of the present invention, include N,N-dimethylformamide, dimethylsulfoxide, lower alcoholic solvents with 1–3 atoms, such as methanol, ethanol and isopropanol, and a mixture thereof.

BEST MODE FOR CARRYING OUT THE INVENTION

The present invention will hereinafter be described in further detail by examples. It should however be borne in mind that the present invention is not limited to or by the examples.

EXAMPLE 1

Preparation of 2-aminopurine, thallium salt 6.75 g (50 mmole) of 2-aminopurine was suspended in 140 ml of anhydrous ethanol, and the temperature of a reactor was maintained below 15° C. The suspension was added slowly with 18.72 g (75 mmole) of thallium (I) ethoxide, followed by stirring for 36 hours at room temperature. At the end of the reaction, the stirred mixture was filtered, and washed with anhydrous ethanol to give 15.57 g (92%) of 2-aminopurine-thallium salt.

Melting point: 290–292° C. (dec.)

IR: νmax (cm$^{-1}$): 3400, 3180, 3060, 2800, 1650, 1580, 1512, 1421

1H NMR (DMSO-d$_6$, 300 MHz) (ppm): 6.35 (2H, brs, —NH$_2$) 8.13 (1H, s, H of C-8) 8.65 (1H, s, H of C-6)

EXAMPLE 2

Preparation of 9-[4-acetoxy-3-(acetoxymethyl)but-1-yl]-2-aminopurine 16.92 g (50 mmole) of 2-aminopurine-thallium salt was suspended in 140 ml of N,N-dimethylformamide, and the temperature of a reactor was maintained below 15° C. The suspension was added slowly with a solution of 16.03 g (60 mmole) of 2-acetoxymethyl-4-bromobut-1-yl-acetate in 30 ml of N,N-dimethylformamide, followed by stirring for 84 hours at room temperature. At the end of the reaction, the stirred mixture was cooled and filtered, and then the filtrate was concentrated under reduced pressure to evaporate the solvent. The residue was purified by silica gel chromatography (CHCl$_3$:MeOH=90:1) to give 9.80 g (61%) of 9-[4-acetoxy-3-(acetoxymethyl)but-1-yl]-2-aminopurine (Rf=0.82).

Melting point: 101–103° C. (dec.)

IR: vmax (cm$^{-1}$): 3330, 3163, 1746, 1729, 1654, 1612, 1582

1H NMR (DMSO-d$_6$, 300 MHz) (ppm): 1.99–1.95 (3H, m, =NCH$_2$CH$_2$CH=) 2.00 (6H, s, —CH(CH$_2$OCOCH$_3$)$_2$) 4.03 (4H, d, —CH(CH$_2$OCOCH$_3$)$_2$) 4.14 (2H, t, =NCH$_2$CH$_2$CH=) 6.45 (2H, brs, —NH$_2$) 8.09 (1H, s, H of C-8) 8.57 (1H, s, H of C-6)

Also, 0.19 g (1.2%) of 7-[4-acetoxy-3-(acetoxymethyl)but-1-yl]-2-aminopurine as a reaction byproduct was obtained (Rf=0.49).

Melting point: 137–139° C.

IR: vmax(cm$^{-1}$): 3330, 3160, 1743, 1728, 1645, 1606

1H NMR (DMSO-d$_6$, 300 MHz) (ppm): 1.86–2.03 (9H, m, =NCH$_2$CH$_2$CH= and —CH(CH$_2$OCOCH$_3$)$_2$) 4.07 (4H, d, —CH(CH$_2$OCOCH$_3$)$_2$) 4.16 (2H, t, =NCH$_2$CH$_2$CH=) 6.38 (2H, brs, —NH$_2$) 8.06 (1H, s, H of C-8) 8.61 (1H, s, H of C-6)

EXAMPLE 3

Preparation of 9-[4-acetoxy-3-(acetoxymethyl)but-1-yl]-2-aminopurine 16.92 g (50 mmole) of 2-aminopurine-thallium salt was suspended in 140 ml of N,N-dimethylformamide, and the temperature of a reactor was maintained below 15° C. The suspension was added slowly with a solution of 16.03 g (60 mmole) of 2-acetoxymethyl-4-bromobut-1-yl-acetate in 30 ml of N,N-dimethylformamide, followed by stirring for 84 hours at room temperature. At the end of the reaction, the stirred mixture was cooled and filtered, and then the filtrate was added with 100 ml of water. The solution was extracted three times with 70 ml of CHCl$_3$, and dried over magnesium sulfate, and then concentrated under reduced pressure to evaporate the solvent. The residue was crystallized from a mixed solvent of ethyl acetate, hexane and tert-butanol, to give 8.35 g (52%) of 9-[4-acetoxy-3-(acetoxymethyl)but-1-yl]-2-aminopurine.

Spectrum data analyzed for the compound obtained in Example 3 were identical to Example 2.

INDUSTRIAL APPLICABILITY

As can be seen from the foregoing, according to the process of the present invention, 9-[4-acetoxy-3-(acetoxymethyl)but-1-yl]-2-aminopurine (called Famciclovir) of Formula (I), a drug of purine derivatives having antiviral activity, can be prepared in a very high selectivity under mild reaction conditions while minimizing the production of 7-[4-acetoxy-3-(acetoxymethyl)but-1-yl]-2-aminopurine of Formula (V) as a reaction byproduct.

The invention claimed is:

1. A process for preparing a compound of Formula (I), which comprises reacting a compound of Formula (XXI) with a compound of Formula (III) in a polar organic solvent:

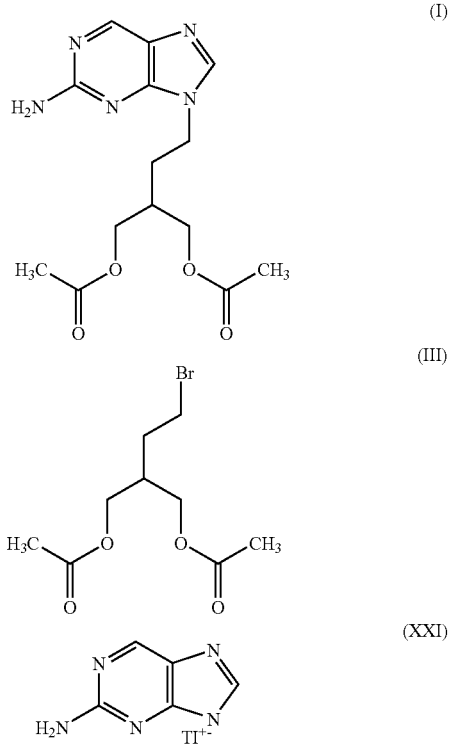

2. The process of claim 1, wherein the polar organic solvent is at least one selected from the group consisting of N,N-dimethylformamide, dimethyl sulfoxide, lower alcoholic solvents with 1–3 carbon atoms, and a mixture thereof.

3. The process of claim 1, wherein the reaction is carried out at a temperature of 0–100° C.

4. The process of claim 2, wherein the reaction is carried out at a temperature of 0–100° C.

* * * * *